United States Patent
McCay et al.

(10) Patent No.: US 6,223,137 B1
(45) Date of Patent: Apr. 24, 2001

(54) METHOD FOR MARKING, TRACKING, AND MANAGING HOSPITAL INSTRUMENTS

(75) Inventors: Mary Helen McCay; T. Dwayne McCay, both of Monteagle; John A. Hopkins, Tullahoma; John Brice Bible, South Pittsburg; Frederick A. Schwartz, Woodbury; Narendra B. Dahotre, Tullahoma; C. Michael Sharp, Belvidere, all of TN (US)

(73) Assignee: The University of Tennessee Research Corporation, Knoxville, TN (US)

( * ) Notice: Subject to any disclaimer, the term of this patent is extended or adjusted under 35 U.S.C. 154(b) by 0 days.

(21) Appl. No.: 09/276,253

(22) Filed: Mar. 25, 1999

(51) Int. Cl.[7] .................................................. G06F 17/60
(52) U.S. Cl. .......................... 702/184; 235/375; 235/285; 705/2
(58) Field of Search .................... 702/184; 235/454, 235/468, 470, 487, 375, 385, 462.21, 900; 705/2; 606/10, 11

(56) References Cited

U.S. PATENT DOCUMENTS

| | | | |
|---|---|---|---|
| 5,035,983 | | 7/1991 | Kiyonari et al. . |
| 5,374,813 | * | 12/1994 | Shipp ................................. 235/375 |
| 5,463,213 | * | 10/1995 | Honda ................................ 235/468 |
| 5,610,811 | * | 3/1997 | Honda ................................... 705/2 |
| 5,637,850 | | 6/1997 | Honda . |
| 5,855,969 | | 1/1999 | Robertson . |

* cited by examiner

Primary Examiner—Marc S. Hoff
Assistant Examiner—Hien Vo
(74) Attorney, Agent, or Firm—Duane, Morris & Heckscher LLP

(57) ABSTRACT

The present invention relates to a method for marking, tracking, and managing hospital instruments. Specifically, the present invention relates to a method for marking instruments with information indicative of the manufacturer, part number, and serial number of each instrument, inputting such information into a database, inputting information into the database regarding the desired maintenance schedule for each instrument, inputting information into the database regarding the usage of each instrument, and tracking the usage and/or maintenance of each instrument by using the information in the database. The method also includes asset management, instrumentation identification and counting, and assembly of surgical trays and kits.

20 Claims, 6 Drawing Sheets

METHOD FOR MARKING, TRACKING, AND MANAGING HOSPITAL INSTRUMENTS

BACKGROUND OF THE INVENTION

1. Field of the Invention

The present invention relates to a method for marking, tracking, and managing hospital instruments. Specifically, the present invention relates to a method for marking instruments with information indicative of the manufacturer, part number, serial number and manufacturing data of each instrument, inputting such information into a database, along with information regarding the desired maintenance schedule, and usage of each instrument, and tracking the usage and/or maintenance of each instrument by using the information in the database. The method also includes asset management, instrumentation identification and counting, and assembly of surgical trays and kits.

2. Description of the Prior Art

It is extremely important to monitor and/or track the use of hospital instruments, particularly instruments used to perform surgery. Large hospitals often comprise many different departments. This multidepartment organizational structure frequently results in nonuniform, rather than centralized, attempts to track the maintenance and/or usage of hospital instruments.

Hospital instruments are expensive and often have short or limited useful lifetimes. The term "hospital instrument", as used herein refers to any instrument or device used for patient care, diagnosis, therapy, or surgery in a hospital or in the office of a physician or surgeon. By way of example, hospital instruments may include, but are not limited to, defibrillators, ultrasonography transducers, and surgical instruments such as forceps. The term "hospital procedure", as used herein, refers to any procedure performed in a hospital or in the office of a physician or surgeon, using a hospital instrument. By way of example, hospital procedures include, but are not limited to, surgery, defibrillation, ultrasound imaging, and magnetic resonance imaging. The costs associated with maintaining and/or replacing hospital instruments are relatively high.

The lack of a centralized system for marking, tracking, and managing hospital instruments can result in unnecessary replacement costs, higher than necessary inventory levels, the failure to perform needed maintenance in a timely manner, or increased exposure to liability resulting from insufficient documentation of maintenance practices. The present invention overcomes the drawbacks of the prior art by providing a centralized system and/or method for marking, tracking, and managing hospital instruments.

Other prior art methods for marking surgical instruments require two separate marking techniques, one technique for surgical instruments having a mirror finish and a second technique for surgical instruments having a nonmirror finish. Such a method is disclosed in U.S. Pat. No. 5,637,850 to Honda. Such dual marking methods are expensive in that they require complex hardware and software capable of distinguishing between the two different types of marking techniques used for different finishes on surgical instruments.

The present invention provides a great advantage over such prior art methods in that a single marking technique is used, regardless of the finish on a hospital instrument. This single marking technique provides economy, not only in the hardware used to mark the hospital instruments, but also in the hardware and software used to read the marks.

SUMMARY OF THE INVENTION

The present invention is directed toward a method for marking and tracking a multiplicity of hospital instruments. This method comprises marking at least two hospital instruments with an optically scannable mark indicative of each instruments manufacturer or service provider and indicative of a serial number unique to each instrument. The invention also comprises reading each mark and entering serial number and manufacturer information represented by each mark into a computer database. The invention further comprises using one or more of the instruments to perform one or more hospital procedures and entering information into the database that identifies each hospital procedure in which each instrument has been used.

The present invention may also be used to identify the sterilization and maintenance on each hospital instrument, identify instrument replacement as required or performed, conduct training, and/or identify the number of usages, repairs, and/or complaints associated with each instrument.

DESCRIPTION OF THE PREFERRED EMBODIMENTS

Figure 4A:
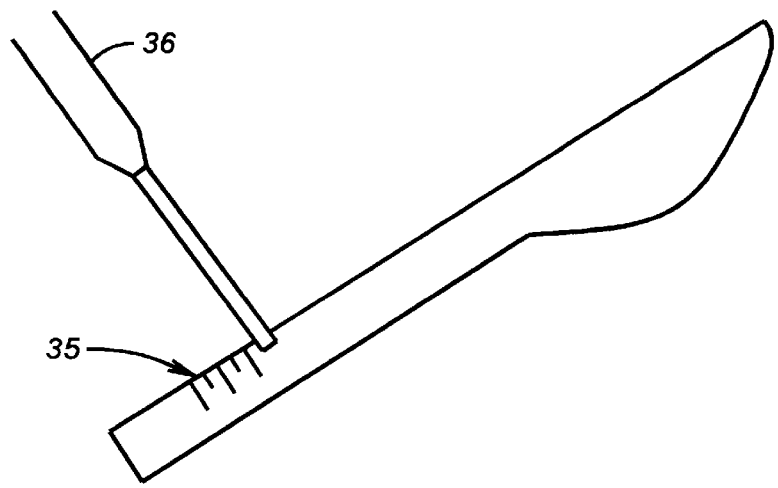
FIG. 4a is a side view of the marking step of the present invention.

A first embodiment of the present invention is directed toward a method for marking and tracking a multiplicity of hospital instruments. This embodiment comprises marking at least two hospital instruments with an optically scannable mark 35 indicative of each instruments manufacturer and indicative of a serial number unique to each instrument, as shown in Block 10 of FIG. 1 and in FIG. 4a. In a preferred embodiment, the marking is performed with a laser 36, as shown in FIG. 4a.

A suitable method for laser marking is laser etching. Laser etching can be used to mark coatings applied to the substrate of a hospital instrument. Pigments may be added to coatings on a hospital instrument in order to effect a color change when the pigments are subjected to a laser in the laser etching process. Suitable pigments for laser etching are available from Infosight Corporation of Chillicothe, Ohio.

Laser bonding is also a suitable method for laser marking many hospital instruments. Laser bonding is a process which involves the bonding of a material to a substrate surface using the heat generated by a laser. Pigments suitable for use with laser bonding are available from Cerdec Corporation of Washington, Pa. In other preferred embodiments, the marking is performed using an ink jet or an acid etch.

The laser marking technique may be laser etching, laser alloying or a combination of laser alloying and laser etching. Laser alloying may be accomplished by coating the selected surface of the hospital instrument to be marked with a thin layer of precursor comprising metallic or ceramic elements suspended in a binder. The precursor coated instrument is then irradiated with a laser in a preselected pattern to form a patterned alloyed surface layer on the instrument. The selection of precursor elements will be a function of the chemical and/or materials composition of the hospital instrument. Alternatively, a selected surface area of the instrument may be irradiated to form a regional alloyed layer or apron. Other marking techniques, such as laser etching, may then be applied to the apron to produce a highly visible and wear resistant mark.

Figure 1:
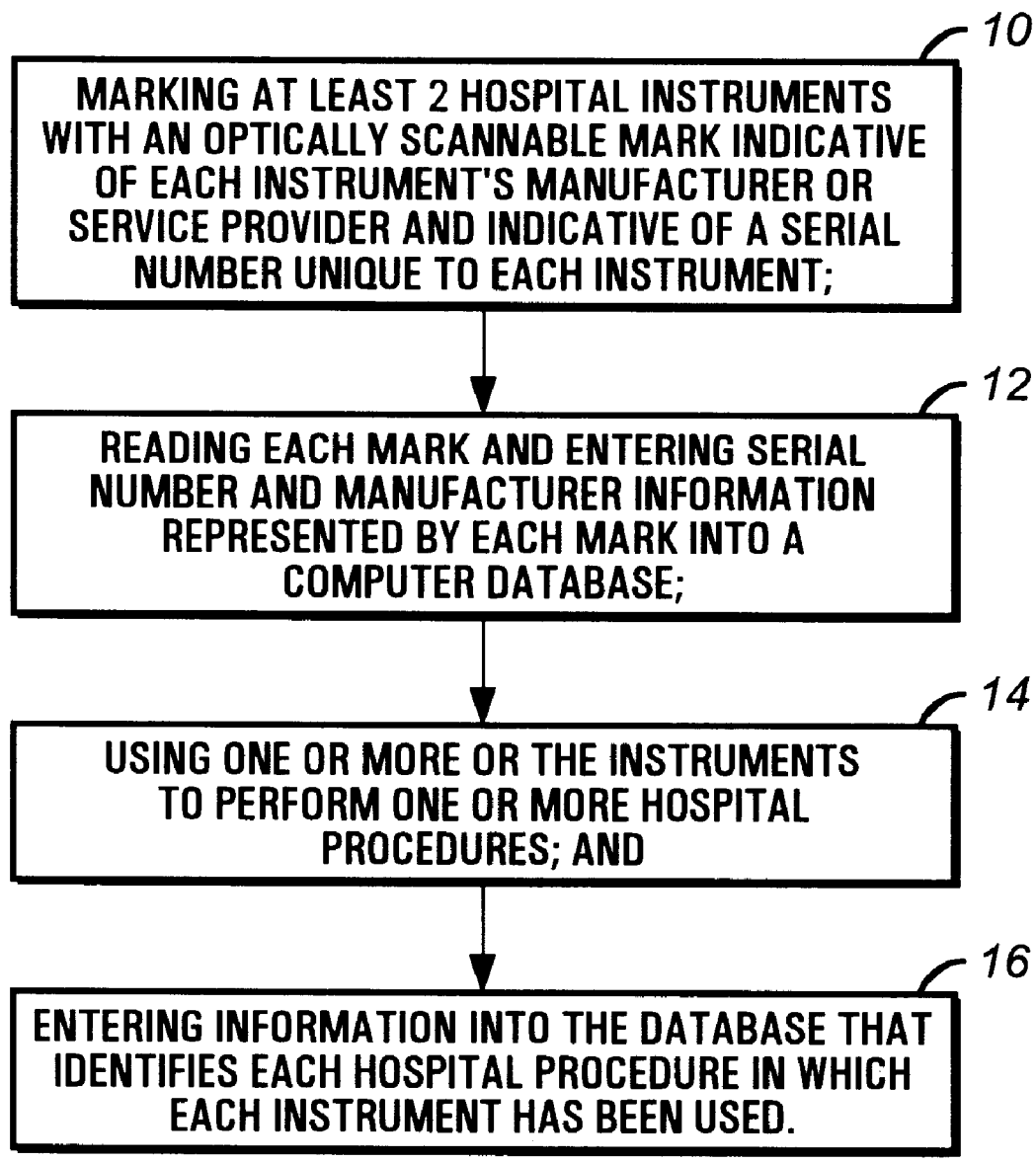
FIG. 1 is a block diagram of a first embodiment of the present invention.
Figure 4B:
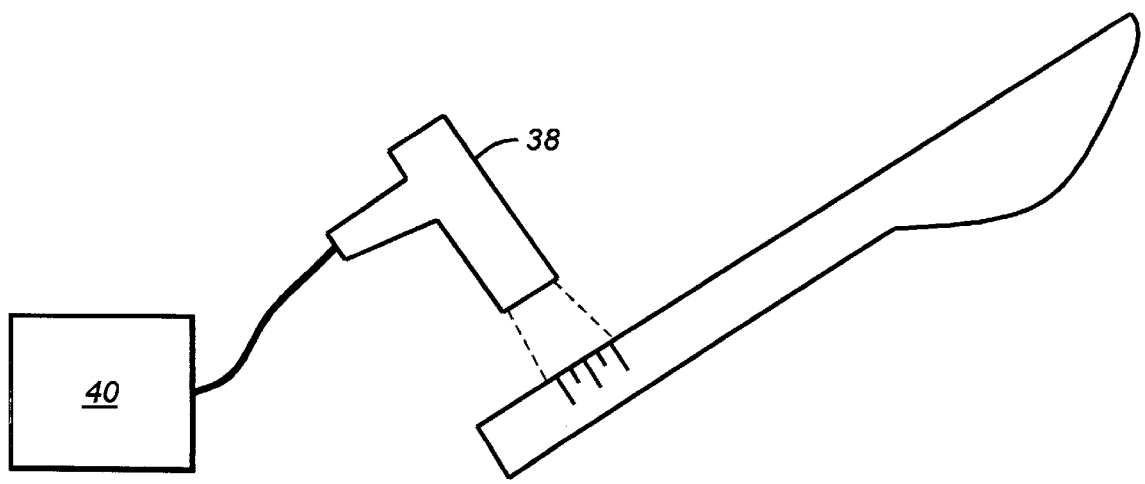
FIG. 4b is a side view of the scanning and entering step of the present invention.

This embodiment of the invention further comprises reading each mark 35 and entering serial number and manufacturer information represented by each mark into a computer database 40 as shown in Block 12 of FIG. 1 and in FIG. 4b.

In a preferred embodiment, the reading and entering comprises scanning with an optical scanner 38 electrically coupled to the database 40. The optical scanner automatically cycles through various lighting schemes and lenses to optimize the image capture. A suitable scanner for use in practicing the present invention is the RVSI MX-1 Handheld Reader, available from RVSI of Canton, Mass.

In another preferred embodiment, the optical scanner is portable, as shown in FIG. 4b. The electrical coupling provides a data transfer path or link between the scanner and the database. The data may also be transferred from the scanner to the database via infrared data transmission methods well known in the art, including Infrared Data Association (IrDA) standards. Other methods of wireless data transfer known in the data communications arts may also be employed in practicing the data entry step of the present invention, including but not limited to RF methods. Other methods of data entry may include voice recordation or terminal entry.

In a preferred embodiment, the database is a relational database. The term "relational database", as used herein, encompasses a database comprising multiple entries, wherein each entry comprises multiple fields of information. In the context of the present invention, it is envisioned that entries will be specific to each instrument. The fields of information on each entry may include manufacturer, part number, serial number, usage history, and/or maintenance history.

In a relational database, information can be stored, sorted, and/or received based upon specified relations between various fields for each entry. For instance, in a relational database for the present invention it will be possible to retrieve entries on all instruments from a specified manufacturer, used in a specific hospital procedure within a specified time period. Such search and retrieval capabilities will facilitate using the present invention to audit instrument maintenance programs. A suitable relational database for use in practicing the present invention is DeRoyal's Meridian Instrument Control System and Pathways Management Module. Another relational database suitable for use in practicing the present invention is the Access database available from Microsoft Corporation of Redmond, Wash.

Figure 3:
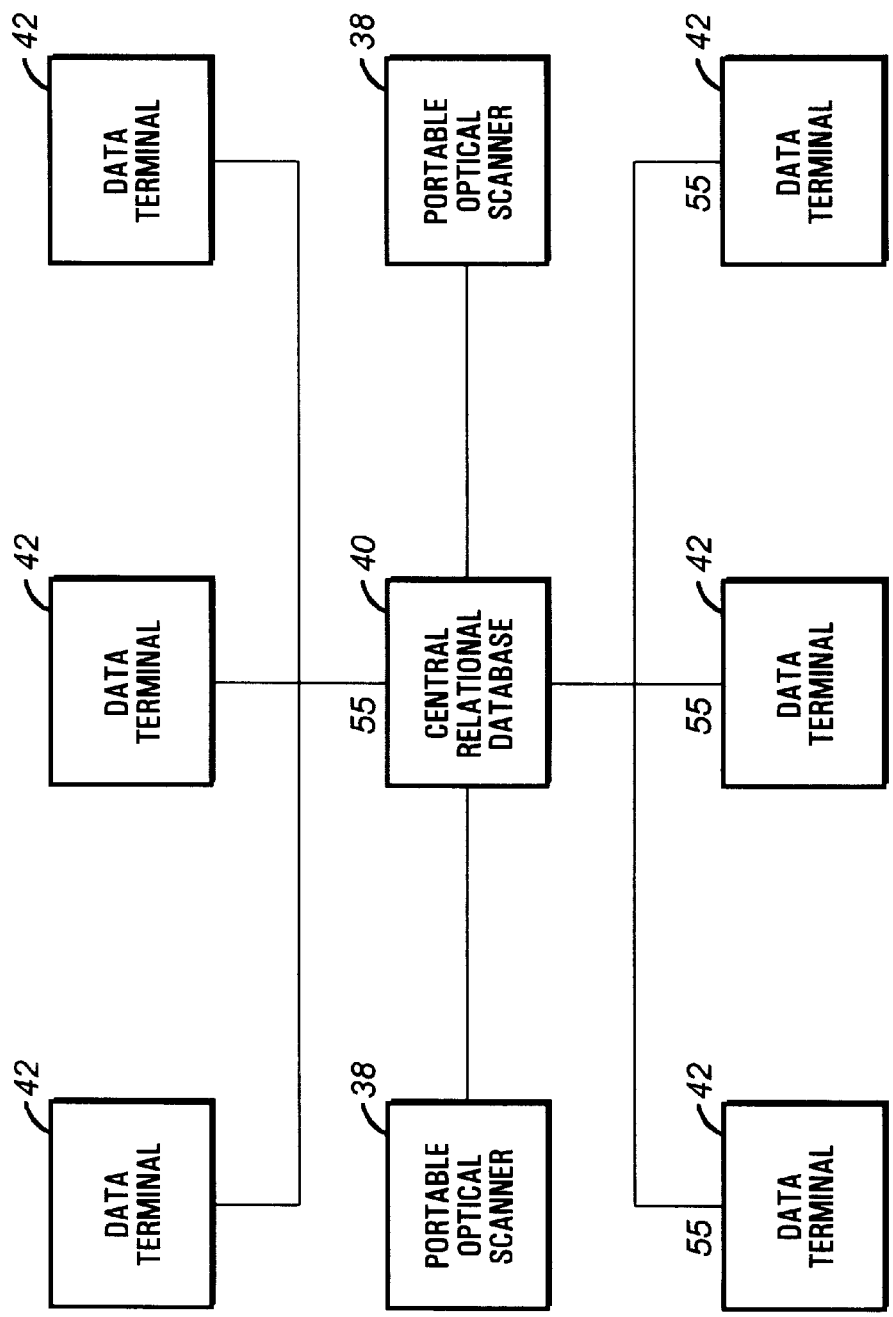
FIG. 3 is a block diagram of a system suitable for practicing the methods of the present invention.

In a preferred embodiment, the database is accessible at multiple data entry and retrieval locations or data terminals 42, as shown in FIG. 3. In another preferred embodiment, the database is accessible in a computer network. The data terminals 42, shown in FIG. 3 may also be computers. In such an embodiment, FIG. 3 illustrates a simplified computer network.

This embodiment of the invention further comprises using one or more of the instruments to perform one or more hospital procedures, as shown in Block 14 of FIG. 1. This embodiment of the invention further comprises entering information into the database that identifies each hospital procedure in which each instrument has been used, as shown in Block 16 of FIG. 1.

Figure 2:
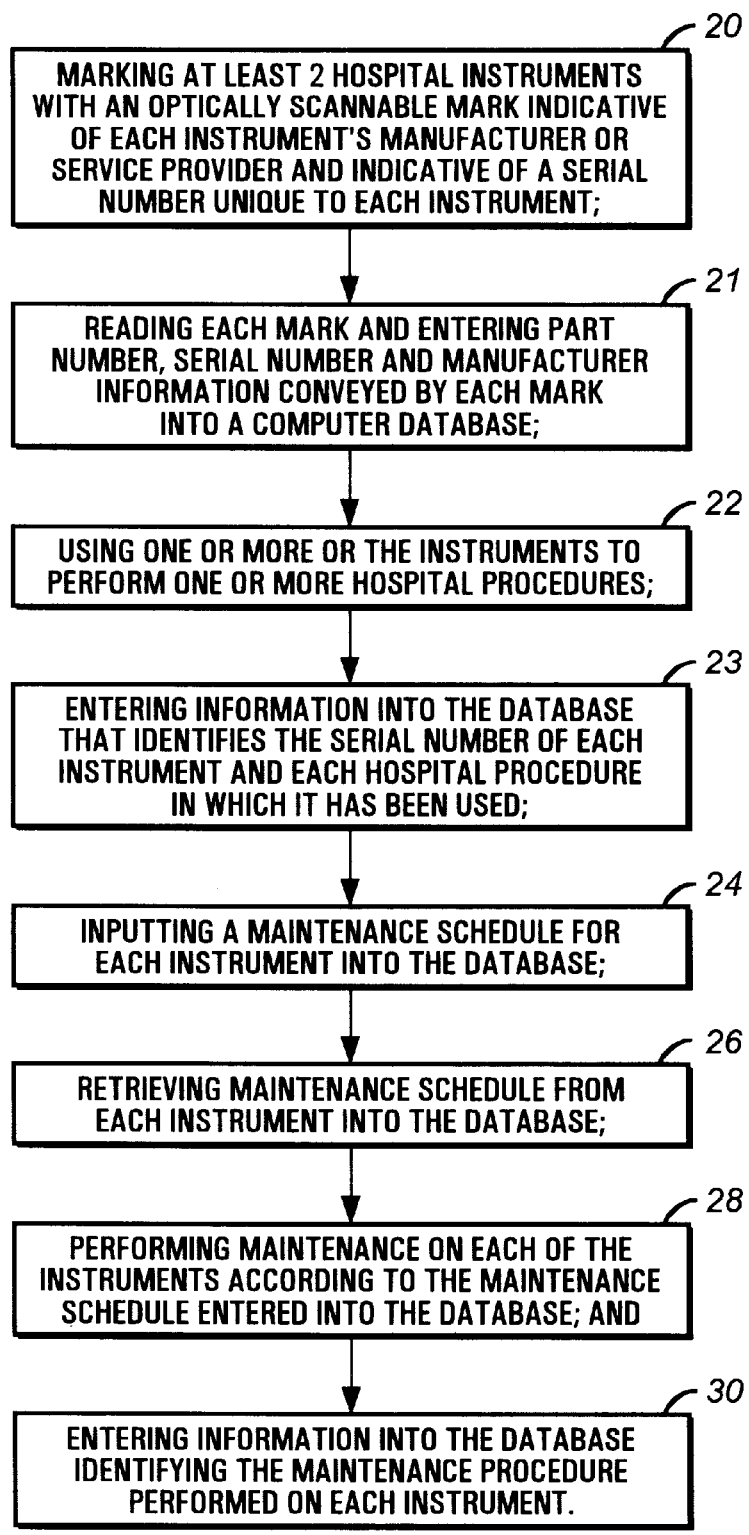
FIG. 2 is a block diagram of a second embodiment of the present invention.

A second embodiment of the present invention is shown in FIG. 2. This embodiment is directed toward a method for marking, tracking, and maintaining a multiplicity of hospital instruments.

It comprises marking at least two hospital instruments with an optically scannable mark indicative of each instrument's manufacturer or service provider and part number, and indicative of a serial number unique to each instrument, as shown in Block 20 of FIG. 2. The term "part number", as used herein, refers to a number unique to each species or type of instrument, such as each trocar or each scalpel. The part number may be used to designate instruments for specified groupings, such as groups of instruments for surgical or hospital kits.

This embodiment of the present invention also comprises reading each mark and entering part number, serial number, and manufacturer or service provider information conveyed by each mark into a computer database, as shown in Block 21 of FIG. 2. In another preferred embodiment, the reading and entering is performed with a portable optical scanner 38 electrically coupled to the computer database, as shown in FIGS. 3 and 4b. The present invention may also be used to scan groups of instruments that are placed in a kit or to identify instruments for sorting into kits. The kit may also be marked, scanned and tracked using the present invention.

This embodiment of the present invention further comprises using one or more of the instruments to perform one or more hospital procedures as shown in Block 22 of FIG. 2, and entering information into the database that identifies the serial number of each instrument and each hospital procedure in which it has been used, as shown in Block 23 of FIG. 2. Hospital procedure information may include an identification of the specific procedure, when it was performed, the nurses/technicians assigned to the procedure, and the surgeons who performed it.

This embodiment of the present invention further comprises inputting a maintenance schedule for each instrument into the database as shown in Block 24 of FIG. 2 and retrieving maintenance schedule information from the database as shown in Block 26 of FIG. 2.

In a preferred embodiment, the retrieving is performed at a data terminal 42 electrically coupled to the database 40, as shown in FIG. 3. The data terminal may be remotely located from the database. The terminal and database may be located in different buildings or in different rooms of the same building.

This embodiment further comprises performing maintenance on each instrument according to the maintenance schedule entered into the database, as shown in Block 28 of FIG. 2. In a preferred embodiment, the invention further comprises entering information into the database identifying the maintenance procedure performed on each instrument, as shown in Block 30 of FIG. 2.

A third embodiment of the present invention is directed toward a method for marking, tracking, and maintaining a multiplicity of hospital instruments and for auditing instrument maintenance. The invention may also be used for determining and tracking replacement requirements and ordering information related to instruments. Such information is particularly useful to a hospital's procurement, or a physician's/surgeon's procurement, office or department. The present invention allows for the selective retrieval of information relevant to determining what replacement instruments should be ordered.

Figure 5A:
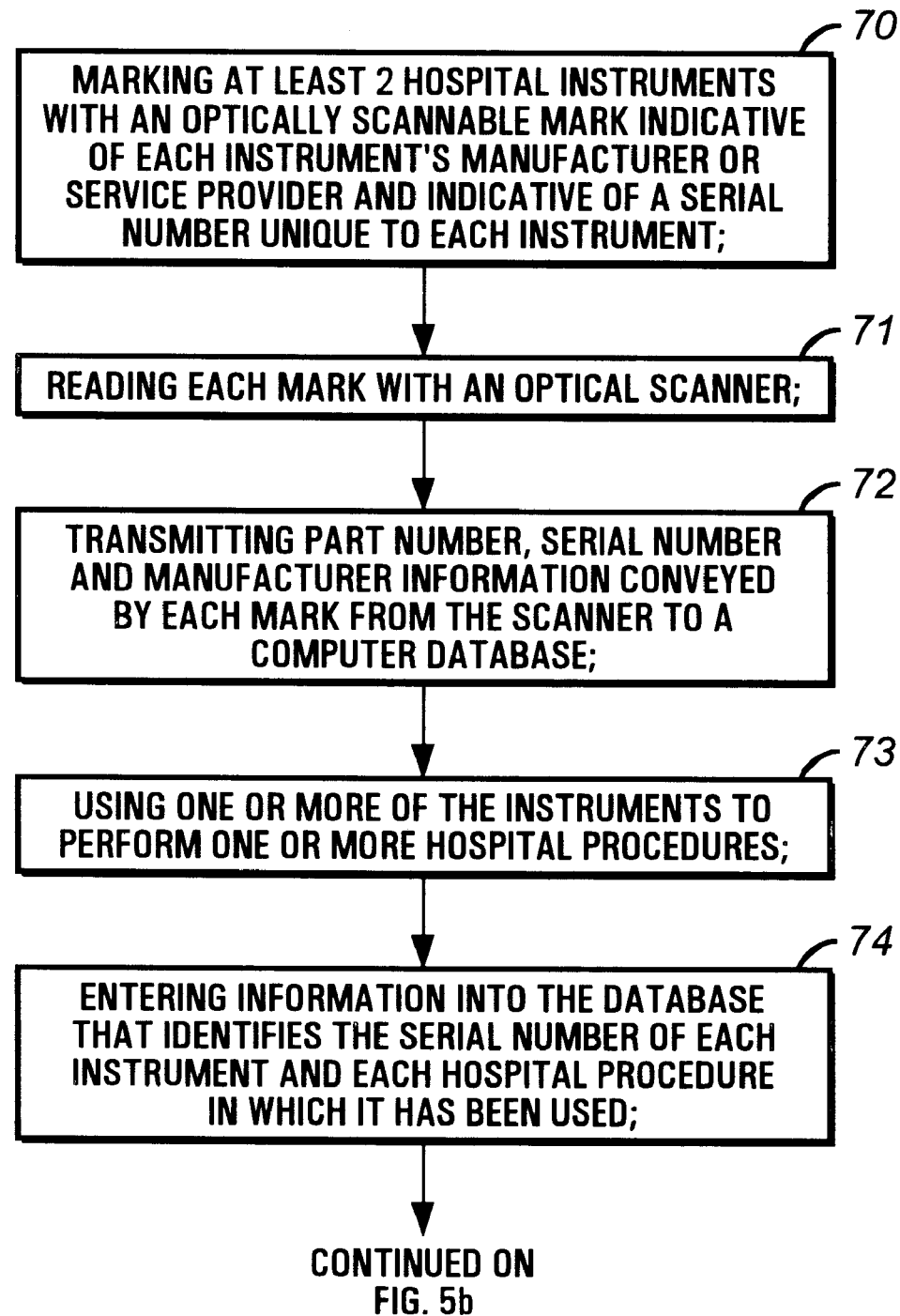
FIGS. 5a–5b are a block diagram of a third embodiment of the present invention.
Figure 5B:
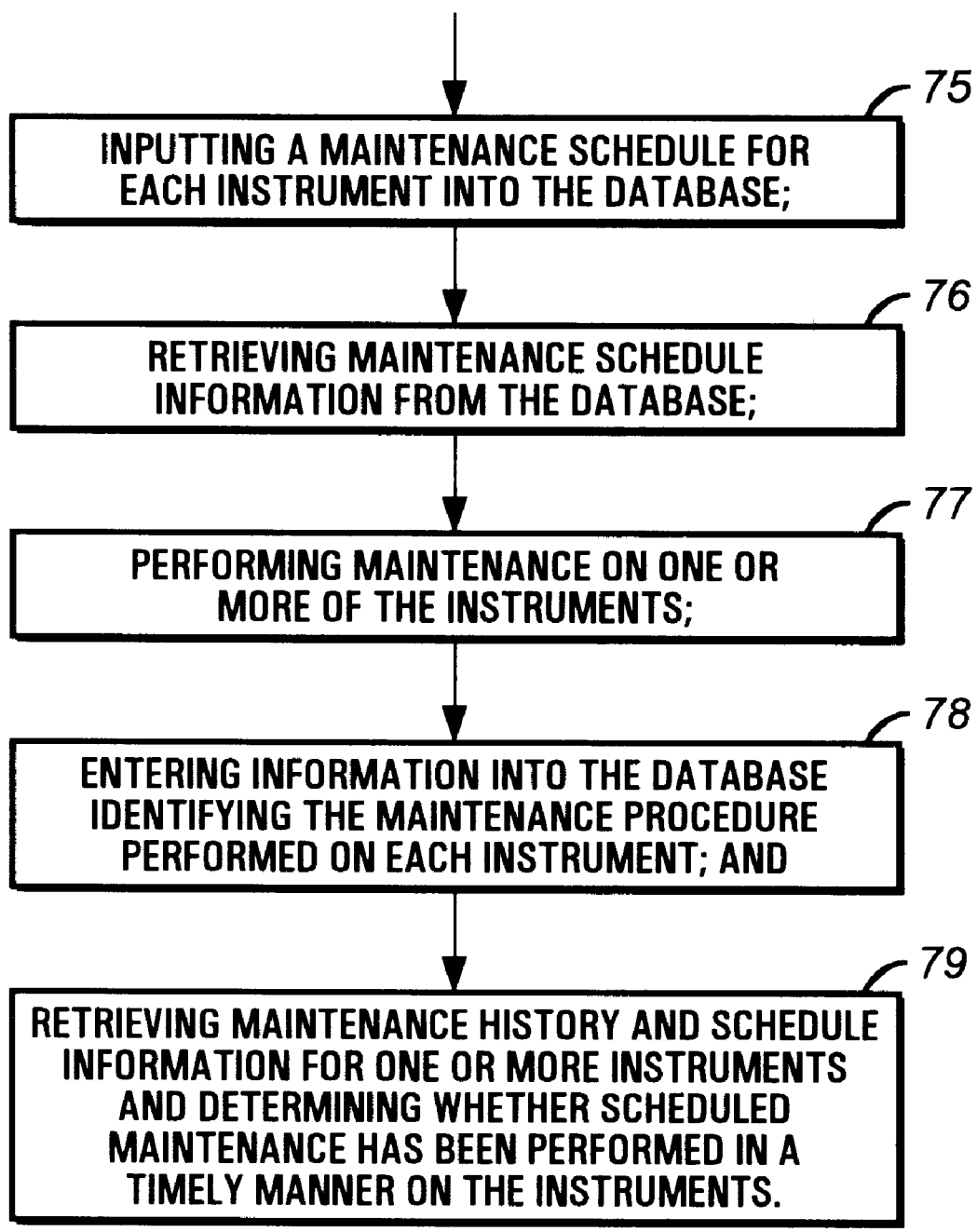

This embodiment is depicted in FIGS. 5a–5b. This method comprises marking at least two hospital instruments with an optically scannable mark indicative of each instrument's manufacturer or service provider and part number, and indicative of a serial number unique to each instrument, as shown in Block 70 of FIG. 5a. The invention further comprises reading each mark with an optical scanner, and transmitting part number, serial number and manufacturer information conveyed by each mark from the scanner to a computer database, as shown in Blocks 71 and 72 of FIG. 5a.

The invention further comprises using one or more of the instruments to perform one or more hospital procedures, and entering information into the database that identifies the serial number of each instrument and each hospital procedure in which it has been used, as shown in Block 73 and 74 of FIG. 5a.

The invention further comprises inputting a maintenance schedule for each instrument into a database, and retrieving maintenance schedule information from the database, as shown in Blocks 75 and 76 of FIG. 5b.

The invention further comprises performing maintenance on one or more of the instruments, and entering information into the database identifying the maintenance procedure performed on each instrument, as shown in Blocks 77 and 78 of FIG. 5b.

The invention also comprises retrieving maintenance history and schedule information on one or more instruments and determining whether scheduled maintenance has been performed in a timely manner on the instruments, as shown in Block 79 in FIG. 5b. This retrieval may take place from a data terminal capable of transmitting data to and receiving data from the database. The terminal may be remotely located from the database and coupled to the database via various data retrieval and/or transfer mechanisms, including, but not limited to, a telephone line 55 or a wireless telecommunication connection comprising a wireless modem, as shown in FIG. 3. This step of the invention provides a mechanism for auditing compliance with the scheduled maintenance program.

The determination of whether scheduled maintenance has been performed in a timely manner can be accomplished by comparing the maintenance schedule for a particular instrument to the maintenance history for the same instrument. The use of a relational database can facilitate the selective retrieval of information for such a comparison.

The foregoing disclosure and description of the invention are illustrative and explanatory. Various changes in the size, shape, and materials, as well as in the details of the illustrative embodiments may be made without departing from the spirit of the invention.

What is claimed is:

1. A method for marking and tracking a multiplicity of hospital instruments comprising:
   a. marking at least 2 hospital instruments with an optically scannable mark indicative of each instrument's manufacturer or service provider and indicative of a serial number unique to each instrument;
   b. reading each mark and entering serial number and manufacturer information represented by each mark into a computer database;
   c. using one or more of the instruments to perform one or more hospital procedures; and
   d. entering information into the database that identifies each hospital procedure in which each instrument has been used.

2. The method of claim 1, wherein said marking is performed with a laser, an ink jet, or an acid etch.

3. The method of claim 1, wherein said reading and entering comprises scanning with an optical scanner electrically coupled to the database.

4. The method of claim 3, wherein the optical scanner is portable.

5. The method of claim 1, wherein each of the scannable marks further comprises information indicative of the part number of each instrument.

6. The method of claim 5, further comprising inputting a maintenance schedule for each instrument into the database.

7. The method of claim 6, further comprising retrieving maintenance schedule information from the database, and performing maintenance on each of said instruments according to the maintenance schedule entered into the database.

8. The method of claim 7, further comprising entering information into the database identifying the maintenance procedure performed on each instrument.

9. The method of claim 1, further comprising entering information into said database specifying the maximum number of permitted uses for each instrument.

10. The method of claim 1, wherein the database is a relational database.

11. The method of claim 1, wherein the database is accessible at multiple data entry and retrieval locations.

12. The method of claim 11, wherein the database is accessible in a computer network.

13. A method for marking, tracking and maintaining a multiplicity of hospital instruments comprising:
   a. marking at least 2 hospital instruments with an optically scannable mark indicative of each instrument's manufacturer or service provider and part number, and indicative of a serial number unique to each instrument;
   b. reading each mark and entering part number, serial number and manufacturer information conveyed by each mark into a computer database;
   c. using one or more of the instruments to perform one or more hospital procedures;
   d. entering information into the database that identifies the serial number of each instrument and each hospital procedure in which it has been used;
   e. inputting a maintenance schedule for each instrument into the database;
   f. retrieving maintenance schedule information from the database; and
   g. performing maintenance on each of the instruments according to the maintenance schedule entered into the database.

14. The method of claim 13, further comprising entering information into the database identifying the maintenance procedure performed on each instrument.

15. The method of claim 13, wherein said part number is indicative of designated instrument groupings.

16. The method of claim 13, wherein said reading and entering is performed with a portable optical scanner coupled to transfer data to said computer database.

17. A method for marking, tracking and maintaining a multiplicity of hospital instruments and for auditing instrument maintenance comprising:
   a. marking at least 2 hospital instruments with an optically scannable mark indicative of each instrument's manufacturer and part number, and indicative of a serial number unique to each instrument;

b. reading each mark with an optical scanner;

c. transmitting part number, serial number and manufacturer information conveyed by each mark from the scanner to a computer database;

d. using one or more of the instruments to perform one or more hospital procedures;

e. entering information into the database that identifies the serial number of each instrument and each hospital procedure in which it has been used;

f. inputting a maintenance schedule for each instrument into the database;

g. retrieving maintenance schedule information from the database;

h. performing maintenance on one or more of the instruments;

i. entering information into the database identifying the maintenance procedure performed on each instrument; and j. retrieving maintenance history and schedule information for one or more instruments and determining whether scheduled maintenance has been performed in a timely manner on the instruments or whether the instrument should be replaced.

18. The method of claim 17 wherein said determining comprises comparing the maintenance schedule for a particular instrument to the maintenance history for the same instrument.

19. The method of claim 17 wherein said database contains information regarding the maximum number of permitted uses for each instrument and said determining comprises comparing the maximum number of permitted uses for a particular instrument to the usage history for the same instrument.

20. The method of claim 17, wherein said retrieving is performed from a data terminal remotely located from the database.

* * * * *

US006223137C1

(12) EX PARTE REEXAMINATION CERTIFICATE (6869th)
United States Patent
McCay et al.

(10) Number: US 6,223,137 C1
(45) Certificate Issued: Jun. 9, 2009

(54) METHOD FOR MARKING, TRACKING, AND MANAGING HOSPITAL INSTRUMENTS

(75) Inventors: Mary Helen McCay, Monteagle, TN (US); T. Dwayne McCay, Monteagle, TN (US); John A. Hopkins, Tullahoma, TN (US); John Brice Bible, South Pittsburg, TN (US); Frederick A. Schwartz, Woodbury, TN (US); Narendra B. Dahotre, Tullahoma, TN (US); C. Michael Sharp, Belvidere, TN (US)

(73) Assignee: The University of Tennessee Research Corporation, Knoxville, TN (US)

Reexamination Request:
 No. 90/008,226, Feb. 9, 2007

Reexamination Certificate for:
 Patent No.: 6,223,137
 Issued: Apr. 24, 2001
 Appl. No.: 09/276,253
 Filed: Mar. 25, 1999

(51) Int. Cl.
 *G09B 23/28* (2006.01)
 *G09B 23/00* (2006.01)
 *G06Q 10/00* (2006.01)

(52) U.S. Cl. .................. 702/184; 235/375; 235/385; 705/2

(58) Field of Classification Search .................. None
 See application file for complete search history.

(56) References Cited

U.S. PATENT DOCUMENTS

| 5,554,841 | A | | 9/1996 | Kost et al. ................ 235/464 |
| 5,560,005 | A | * | 9/1996 | Hoover et al. ............. 707/10 |
| 2006/0244593 | A1 | * | 11/2006 | Nycz et al. .............. 340/572.1 |

OTHER PUBLICATIONS

Theo Haerder "Implementing a Generalized Access Path Structure for a Relational Database System" (ACM Transactions on Database Systems, vol. 3, No. 3, Sep. 1978, pp. 285–298.*
Shaw, Kathleen, "Scanning the Future of Surgical Instrument Instrument Inventories with Dr. William Fry and the Surgical Instrument Inventory System", M.D. News, Apr. 1996, pp. 1–3.*

* cited by examiner

*Primary Examiner*—Anjan K. Deb

(57) ABSTRACT

The present invention relates to a method for marking, tracking, and managing hospital instruments. Specifically, the present invention relates to a method for marking instruments with information indicative of the manufacturer, part number, and serial number of each instrument, inputting such information into a database, inputting information into the database regarding the desired maintenance schedule for each instrument, inputting information into the database regarding the usage of each instrument, and tracking the usage and/or maintenance of each instrument by using the information in the database. The method also includes asset management, instrumentation identification and counting, and assembly of surgical trays and kits.

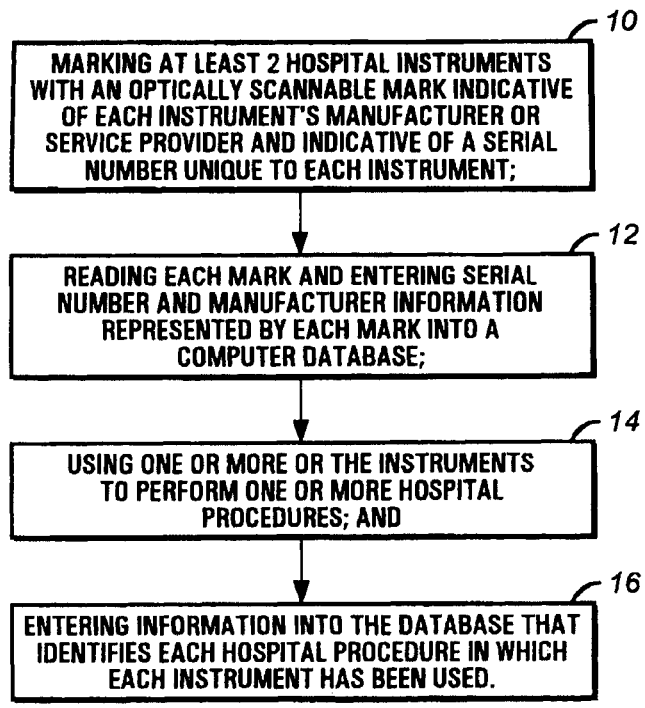

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 3 and 16 are cancelled.

Claims 1, 4, 5, 13 and 17 are determined to be patentable as amended.

Claims 2, 6–12, 14–15 and 18–20, dependent on an amended claim, are determined to be patentable.

New claims 21–25 are added and determined to be patentable.

1. A method for marking and tracking a multiplicity of hospital instruments comprising:
    a. marking at least 2 hospital instruments with an optically scannable mark [indicative of] *comprising information conveying* each instrument's manufacturer or service provider and [indicative of] *comprising information conveying* a serial number unique to each instrument;
    b. reading each mark *by scanning each mark with an optical scanner* and [entering] *transmitting* serial number and manufacturer information [represented] *conveyed* by each mark *from the scanner* into a computer database;
    c. using one or more of the instruments to perform one or more hospital procedures; and
    d. entering information into the database that identifies each hospital procedure in which each instrument has been used.

4. The method of claim [3] *1*, wherein the optical scanner is portable.

5. The method of claim 1, wherein each of the scannable marks further comprises information [indicative of] *conveying* the part number of each instrument.

13. A method for marking, tracking and maintaining a multiplicity of hospital instruments comprising:
    a. marking at least 2 hospital instruments with an optically scannable mark [indicative of] *comprising information conveying* each instrument's manufacturer or service provider and part number, and [indicative of] *comprising information conveying* a serial number unique to each instrument;
    b. reading each mark *by scanning each mark with an optical scanner* and [entering] *transmitting* part number, serial number and manufacturer information conveyed by each mark *from the scanner* into a computer database;
    c. using one or more of the instruments to perform one or more hospital procedures;
    d. entering information into the database that identifies the serial number of each instrument and each hospital procedure in which it has been used;
    e. inputting a maintenance schedule for each instrument into the database;
    f. retrieving maintenance schedule information from the database; and
    g. performing maintenance on each of the instruments according to the maintenance schedule entered into the database.

17. A method for marking, tracking and maintaining a multiplicity of hospital instruments and for auditing instrument maintenance comprising:
    a. marking at least 2 hospital instruments with an optically scannable mark [indicative of] *comprising information conveying* each instrument's manufacturer and part number, and [indicative of] *comprising information conveying* a serial number unique to each instrument;
    b. reading each mark with an optical scanner;
    c. transmitting part number, serial number and manufacturer information conveyed by each mark from the scanner to a computer database;
    d. using one or more of the instruments to perform one or more hospital procedures;
    e. entering information into the database that identifies the serial number of each instrument and each hospital procedure in which it has been used;
    f. inputting a maintenance schedule for each instrument into the database;
    g. retrieving maintenance schedule information from the database;
    h. performing maintenance on one or more of the instruments;
    i. entering information into the database identifying the maintenance procedure performed on each instrument; and
    j. retrieving maintenance history and schedule information for one or more instruments and determining whether scheduled maintenance has been performed in a timely manner on the instruments or whether the instrument should be replaced.

*21. The method of claim 1, wherein in step d. the information entered into the database includes:*

*an identification of the specific procedure performed;*

*an identification of when the specific procedure was performed;*

*an identification of the nurses or technicians assigned to the specific procedure; and*

*an identification of the surgeon or surgeons who performed the specific procedure.*

*22. The method of claim 1, further comprising:*

*placing the instruments of step a. in a kit;*

*marking the kit with an optically scannable mark;*

*scanning the mark on the kit; and*

*tracking the kit.*

*23. The method of claim 1, wherein:*

*the database is a relational database comprising multiple entries, each entry comprising multiple fields of information including manufacturer, serial number, usage history and maintenance history, wherein the relational database permits the information to be stored, sorted and received based upon specified relations between the multiple fields of information.*

*24. The method of claim 1, further comprising:*

*inputting a maintenance schedule for each instrument into the database;*

*retrieving the maintenance schedule information from the database; and*

*performing maintenance on each of the instuments according to the maintenance schedule entered into the database.*

25. *The method of claim 1, further comprising:*

*inputting a maintenance schedule for each instrument into the database;*

*performing maintenance on one or more of the instruments;*

*entering information into the database identifying the maintenance procedure performed on each instrument; and*

*retrieving maintenance history and schedule information for one or more instruments and determining whether scheduled maintenance has been performed in a timely manner on the instruments or whether the instrument should be replaced.*

\* \* \* \* \*